(12) United States Patent
D'Gama et al.

(10) Patent No.: US 9,796,536 B2
(45) Date of Patent: Oct. 24, 2017

(54) AUTOMATIC GEMSTONE ORIENTATION

(75) Inventors: Siobhan D'Gama, London (GB); Maxwell Ralph Willis, Oxfordshire (GB); Nicholas Matthew Davies, Berkshire (GB); Graham Ralph Powell, Berkshire (GB)

(73) Assignee: DE BEERS UK LTD., London (GB)

( * ) Notice: Subject to any disclaimer, the term of this patent is extended or adjusted under 35 U.S.C. 154(b) by 245 days.

(21) Appl. No.: 14/114,025

(22) PCT Filed: Apr. 20, 2012

(86) PCT No.: PCT/GB2012/050878
§ 371 (c)(1),
(2), (4) Date: Jan. 15, 2014

(87) PCT Pub. No.: WO2012/146913
PCT Pub. Date: Nov. 1, 2012

(65) Prior Publication Data
US 2014/0119613 A1 May 1, 2014

(30) Foreign Application Priority Data
Apr. 26, 2011 (GB) .................................. 1106878.0

(51) Int. Cl.
*B65G 47/244* (2006.01)
*G01N 21/87* (2006.01)
(Continued)

(52) U.S. Cl.
CPC ........... *B65G 47/244* (2013.01); *G01N 21/87* (2013.01); *G06T 7/70* (2017.01); *G01N 33/381* (2013.01)

(58) Field of Classification Search
CPC .................................................. B65G 47/244
(Continued)

(56) References Cited

U.S. PATENT DOCUMENTS 4,010,778 A * 3/1977 Aggen ..................... A01C 7/16
111/200
4,288,398 A * 9/1981 Lemelson ............... B21C 31/00
264/443
(Continued)

FOREIGN PATENT DOCUMENTS

BE 892-777 A1 8/1982
BE 1013663 A6 5/2002
(Continued)

OTHER PUBLICATIONS

English translation of Japanese Office Action dated Dec. 22, 2015 for corresponding Japanese Application No. 2014-506930.
(Continued)

*Primary Examiner* — Leslie A Nicholson, III
*Assistant Examiner* — Lester Rushin
(74) *Attorney, Agent, or Firm* — Renner, Otto, Boisselle & Sklar, LLP

(57) ABSTRACT

A method and apparatus for orientating discrete objects, such as gemstones, is described. The method comprises providing the objects on a travelling path; providing a pair of opposed walls (38) extending generally along the direction of the path; and generating relative oscillatory movement (14) between the pair of walls (38) and the travelling path (in a direction generally transverse to the direction of the path), so that the pair of walls (38) imparts lateral force to the objects to thereby urge them into their most stable orientation as they progress along the path. A device for checking the orientation of the discrete objects is also described.

33 Claims, 6 Drawing Sheets

(51) Int. Cl.
*G06T 7/70* (2017.01)
*G01N 33/38* (2006.01)

(58) Field of Classification Search
USPC .......................................... 198/394.047, 394
See application file for complete search history.

(56) References Cited

U.S. PATENT DOCUMENTS

| | | | |
|---|---|---|---|
| 5,015,090 A | | 5/1991 | Weisman |
| 5,172,800 A | * | 12/1992 | Brown ............... B65G 47/2445 198/380 |
| 5,193,685 A | | 3/1993 | Trevithick |
| 5,235,815 A | * | 8/1993 | Nielson .................. C01B 31/20 62/637 |
| 7,041,926 B1 | | 5/2006 | Gadberry |
| 2003/0227617 A1 | | 12/2003 | Yoshida et al. |
| 2005/0168758 A1 | | 8/2005 | Hayasaki et al. |
| 2008/0134640 A1 | * | 6/2008 | Bowden ............... B65B 11/025 53/432 |
| 2009/0151305 A1 | * | 6/2009 | Cassoni ............... B67B 3/0645 53/485 |
| 2010/0133066 A1 | * | 6/2010 | Bassini .................... B65B 5/08 198/460.1 |

FOREIGN PATENT DOCUMENTS

| | | | |
|---|---|---|---|
| DE | 12 80 728 B | | 10/1968 |
| DE | 1280728 B | * | 10/1968 ......... B65G 47/1492 |
| DE | 4026691 A1 | | 2/1992 |
| EP | 1279628 A1 | | 1/2003 |
| EP | 2 381 215 A1 | | 10/2011 |
| GB | 1 380 383 A | | 1/1975 |
| GB | 2 081 439 A | | 2/1982 |
| GB | 2 134 090 A | | 8/1984 |
| GB | 2 162 828 A | | 2/1986 |
| GB | 2 194 518 A | | 3/1988 |
| GB | 2 194 779 A | | 3/1988 |
| JP | 44-007616 | | 3/1969 |
| JP | 56-098816 | | 8/1981 |
| JP | 03-038819 | | 2/1991 |
| JP | 2004-067360 A | | 3/2004 |
| JP | 2007-233780 A | | 9/2007 |
| JP | 2009-102106 | | 5/2009 |
| JP | 2009-250680 | | 10/2009 |
| WO | WO 00/28309 | | 5/2000 |
| WO | WO 00/48930 A1 | | 8/2000 |
| WO | WO 2011/037481 A1 | | 3/2011 |

OTHER PUBLICATIONS

English translation of Russian Notification for corresponding Russian Application No. 2013151383/28(080156).
International Search Report for corresponding International Application No. PCT/GB2012/050878 dated Sep. 19, 2012.
Form PCT/ISA/237 for corresponding International Application No. PCT/GB2012/050878 dated Sep. 19, 2012.
British Search Report for corresponding British Application No. GB1106878.0 dated Jul. 5, 2011.
British Search Report for corresponding British Application No. GB1106878.0 dated Nov. 29, 2011.
Korean Examination and Search Report dated Oct. 23, 2016 for corresponding Korean Application No. UAE/P/ 1087/2013.

* cited by examiner

AUTOMATIC GEMSTONE ORIENTATION

FIELD OF THE INVENTION

This invention relates to automatic gemstone orientation. Particularly, but not exclusively, the invention relates to a method of orientating discrete objects, such as gemstones, for subsequent handling and/or measurement. An apparatus for orientating and screening such discrete objects is also provided.

BACKGROUND TO THE INVENTION

The screening of diamonds (and other gemstones) is required in order to distinguish synthetic materials from those that are natural. It is known that, in an unpolished state, High-Pressure, High-Temperature (HPHT) synthetic diamonds have distinctive cubo-octahedral shapes which make them easy to distinguish from natural diamonds which grow in an octahedral form. Even when synthetic material is polished into a gemstone, identification is still possible. In certain cases, identification can be adequately performed by looking for metallic inclusions and colour-zoning (where colour is more concentrated in certain geometric zones) using a microscope. However, in order to identify synthetics having better quality and colour more advanced instrumentation such as the Applicants' DiamondSure™ and DiamondView™ instruments may be required.

The DiamondSure™ instrument is a rapid, easy to use, screening instrument which measures the way light is absorbed by a diamond in order to identify synthetics. The diamond under test may either be passed, if it is a natural, or referred for further tests, if the stone needs to be looked at more closely. It has been found that this instrument refers all synthetics and around 2% of natural diamonds (which are susceptible to a colour treatment) for further testing.

The referred diamonds are then analysed using the DiamondView™ instrument which generates a surface fluorescent image of the stone using intense short-wave ultraviolet lamps. As synthetics typically show distinct geometric patterns from their characteristic growth sectors, these can quickly be identified.

However, as the diamonds are required to be in a particular orientation for each of the above screening processes, it has, to date, been necessary for each individual diamond to be manually placed on the screening equipment. There is therefore a need for automatic gemstone orientation in order to speed up this procedure.

SUMMARY OF THE INVENTION

According to a first aspect of the present invention there is provided a method of orientating discrete objects, such as gemstones, said method comprising:
   providing said objects on a travelling path;
   providing a pair of opposed walls extending generally along the direction of the path; and
   generating relative oscillatory movement between said pair of walls and said travelling path, in a direction generally transverse to the direction of the path, so that said pair of walls imparts lateral force to the objects to thereby urge them into their most stable orientation as they progress along the path.

Embodiments of the present invention therefore provide a process which can be automated for fast and effective orientation of a number of discrete objects. It will be understood that the lateral force provided by the oscillating walls will effectively and progressively knock the objects from a relatively unstable orientation into a relatively stable orientation. Accordingly, the objects may be urged into an orientation in which they have their lowest potential energy (i.e. in which their centre of mass is at its lowest point).

The discrete objects may comprise cut or uncut gemstones (e.g. diamonds) or other small items. In particular embodiments, the discrete objects may comprise so-called melee (i.e. small, usually brilliant cut diamonds, normally between 0.01 and 0.20 carats each and which are often used as side stones and in pave settings). In other embodiments, larger diamonds up to or greater than 1 carat (ct) may be employed. However, it is noted that the method described above is particularly useful for the orientation of small diamonds (e.g. less than approximately 1 ct) since, manual orientation of larger diamonds is less fiddly and time-consuming.

In embodiments of the invention, the melee may be pre-sized into parcels where the difference in girdle diameters can vary by up to 0.5 mm. The method may then comprise the step of dispensing the melee onto the travelling path at an appropriate feed rate.

In the case of cut gemstones it is common for one facet to be polished to form a so-called table which can be used for mounting the gem for measurement, further processing or polishing. The table is usually the largest cut facet and orientation on the table therefore corresponds to the gemstone being positioned in its deepest potential well. The gem is therefore normally in its most stable and convenient orientation when it is positioned table-down on a supporting surface.

The travelling path may be circular and the relative oscillatory movement may be such that a central portion of the pair of walls oscillates along a radius of the travelling path. A particularly advantageous embodiment can be provided by employing a part-circular (and in particular, semi-circular) pair of walls because the objects will experience only a small amount of lateral movement as they enter the pair of walls and this will gradually increase towards the centre of the pair of walls, where the transverse movement is at its greatest, before the amount of lateral movement reduces once more towards the exit from the pair of walls. Accordingly, the lateral movement of the objects is better controlled and contained within the pair of walls since the objects are effectively accelerated from and decelerated to a stationery start and end point on the travelling path, within the confines of the walls. There is therefore a much lower risk of the objects being inadvertently ejected from between the pair of walls than if they were experiencing the full transverse movement of the walls as they entered or exited the walls (e.g. as would be the case on a straight travelling path).

The method may further comprise the step of checking the orientation of each of the objects. This step may be performed after the objects have emerged from between the pair of walls.

The step of checking the orientation of each object may comprise:
   obtaining an image of the object;
   converting the image into a binary silhouette;
   plotting the number of pixels representing the object in each row against row number;
   fitting an expected curve to the plotted data;
   calculating the error between the fitted curve and the plotted data; and
   determining whether the error is within a pre-determined threshold denoting that the object is orientated as desired.

The expected curve may comprise a straight line. In the case of a gemstone, table-down orientation is usually required and this can be determined using a straight line fit to the plotted data.

The method may further comprise the step of sending the object along the travelling path for a second or subsequent time, if the object is determined not to be orientated as desired (i.e. if the error is greater than the pre-determined threshold).

The method may further comprise the step of adjusting the oscillation frequency based on information obtained during the step of checking the orientation of each object. For example, the frequency may be varied if a pre-determined number of objects are determined to be incorrectly orientated or if the calculated error exceeds a pre-determined value.

The method may further comprise the step of transporting the objects that are orientated as desired to a test, measurement or further processing (e.g. polishing) station. The method may then comprise performing a test, measurement or processing procedure. The procedure may comprise determining whether the object is synthetic or natural (e.g. using a DiamondSure™ or DiamondView™ instrument). The method may then comprise dispensing the object into an appropriate receptacle (e.g. into a receptacle for synthetics or a receptacle for naturals) depending on the outcome of the procedure.

According to a second aspect of the present invention there is provided an apparatus for orientating discrete objects, such as gemstones, said apparatus comprising:
  a movable surface providing a travelling path for said objects;
  a pair of opposed walls extending generally along the direction of the path; and
  an oscillator arranged to generate relative oscillatory movement between said pair of walls and said movable surface, in a direction generally transverse to the direction of the path, so that, in use, said pair of walls imparts lateral force to the objects to thereby urge them into their most stable orientation as they progress along the path.

The apparatus may further comprise a device for checking the orientation of the objects (e.g. after they emerge from between the pair of walls).

The movable surface may be translatable (e.g. in the form of a linear conveyer belt) or rotatable (e.g. in the form of a rotatable disc). In a particular embodiment, the movable surface may be constituted by a rotatable platform. The platform may be circular (i.e. disc-shaped) or any other convenient shape.

It will be understood that, depending on the nature of the movable surface, the path for the objects to travel along may be substantially straight, curved, circular, part-circular or semi-circular. However, as explained above, the applicants have discovered that it is advantageous to provide a curved or at least part-circular path since objects travelling along such a path are less likely to be thrown off the path when emerging from between the pair of relatively oscillating walls, than is the case if the path is substantially straight. Continuous paths, as provided by circular paths, are particularly advantageous because the objects can more easily be placed on and removed from the path as there is no defined start and end of the path to be managed. Moreover, with continuous (e.g. circular) paths, objects that are not sufficiently orientated after going around the path once can simply be left on the movable surface to go around again.

The oscillator may be arranged such that a central portion of the pair of walls oscillates along a radius of the rotatable disc.

The moveable surface may have a relatively low coefficient of friction to allow the objects to be re-orientated on contact with at least one of the pair of walls.

The pair of walls may be interconnected. The pair of walls may be substantially vertical or may curve inwardly towards each other. Where the movable surface is a rotatable disc, the pair of walls may be part-toroidal and may extend around approximately half of the disc.

The applicants have found that an optimum oscillation rate and oscillation distance is dependent on the size of the objects to be orientated. The oscillator may therefore be configured to provide an oscillation rate and distance which has been pre-determined as optimum in order to orientate a specific size (or weight) of object. In other embodiments, the oscillator may be configured to provide a range of oscillation rates and/or distances or a variable oscillation rate and/or distance.

The apparatus may further comprise a feeder for providing the objects on the movable surface. The feeder may comprise a hopper arranged to dispense the objects onto the movable surface. The hopper may be configured to space out the objects along the travelling path so that the risk of the objects coming into contact with each other as they are agitated by the oscillator is minimised. In certain embodiments, the feeder may be of the type described in one or more of the UK patents GB 2162828, GB 2194518 or GB 2194779.

The apparatus may comprise a handler configured for transporting the objects from the movable surface after they have passed between the pair of walls at least once. The handler may comprise a vacuum wand configured to latch onto and hold said objects in a particular orientation. The handler may be configured to only transport those objects identified as being correctly orientated by the device. The handler may be configured to place the objects on a further piece of equipment, such as a test or measurement device, gemstone grading apparatus, jewellery or gemstone manufacturing or inscription equipment, gemstone viewer or imaging device or a polisher. More specifically, the handler may place the objects on a synthetic detection device which may comprise a Fourier Transform Infrared (FTIR) Spectrometer. In particular embodiments, the handler may place the objects on one of the DiamondSure™ or DiamondView™ instruments described above. The objects may then be tested or further processed before the handler transports them to an appropriate receptacle or collection point.

In embodiments of the invention, the apparatus may comprise a selector (e.g. dial) allowing the operator to select an appropriate object (e.g. melee) size range which may be based on girdle diameter or respective weight. The selected size range may then be used to define the speed of one or more characteristics of the apparatus (e.g. the speed by which the objects are delivered, rotated, oscillated, handled or dispensed).

In embodiments of the present invention, the apparatus may be constituted by an automated melee screening machine which is coupled to a device configured for the automatic detection of synthetic objects and which employs the feed, handling & dispense processes described above to screen a large volume of small objects, such as gemstones, at an increased rate. Following initial setup by an operator, the applicants have found that the apparatus can be left to run unattended and can sort volumes of up to 500 very small polished round brilliant stones in approximately 30 minutes.

The apparatus may therefore be configured to provide objects to a detection device at a feed rate of approximately 15 objects per minute.

According to a third aspect of the present invention there is provided a device for checking the orientation of discrete objects, such as gemstones, said device comprising:
an image capture module arranged to obtain an image of the object; and
a processor configured for:
converting the image into a binary silhouette;
plotting the number of pixels representing the object in each row against row number,
fitting an expected curve to the plotted data,
calculating the error between the fitted curve and the plotted data; and
determining whether the error is within a pre-determined threshold denoting that the object is orientated as desired.

According to a fourth aspect of the present invention there is provided an apparatus for screening for artificial gemstones, said apparatus comprising:
the apparatus for orientating discrete objects in accordance with the first aspect if the invention;
a feeder for providing gemstones on the movable surface;
a test device for determining whether the gemstones are artificial; and
a handler for transporting the gemstones to the test device and subsequently transporting the gemstones to an appropriate receptacle or collection point.

The apparatus may further comprise a device for checking the orientation of the gemstones, such as the device in accordance with the third aspect of the invention.

It will be understood that the features described above in relation to any one of the aspects of the invention may be mixed and matched with features from any of the other aspects of the invention.

BRIEF DESCRIPTION OF THE DRAWINGS

Specific embodiments of the various aspects of the present invention are described in more detail below in relation to the accompanying drawings, in which.

DETAILED DESCRIPTION OF CERTAIN EMBODIMENTS

Figure 1:
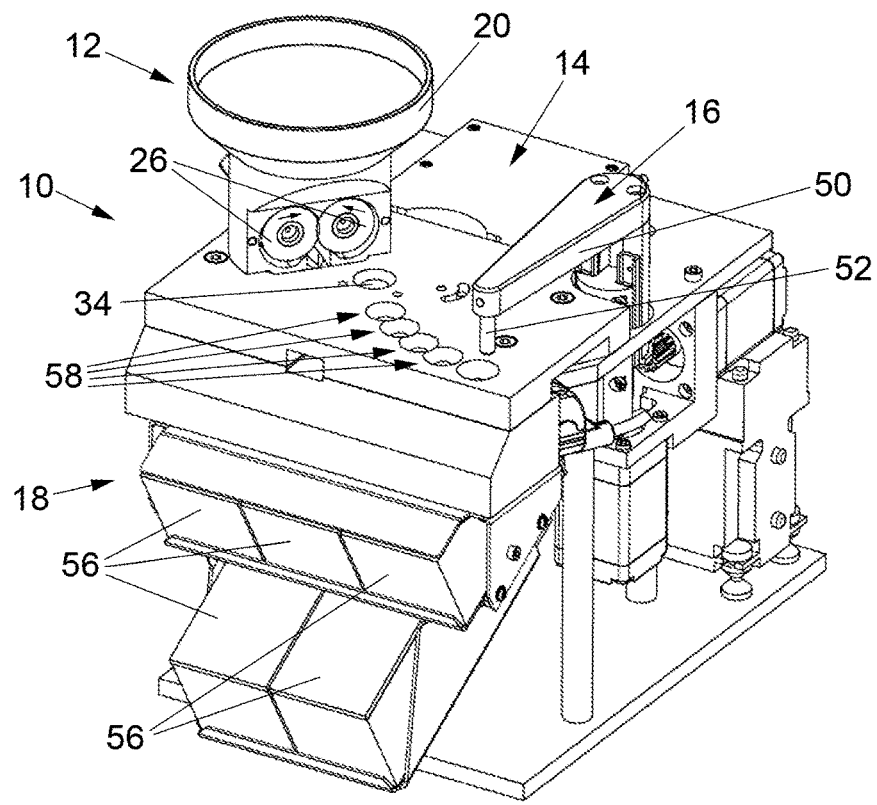
FIG. 1 illustrates a front perspective view of an apparatus for orientating discrete objects in accordance with a first embodiment of the present invention.

With reference to FIG. 1, there is illustrated an apparatus 10 for orientating discrete objects (not shown) in accordance with a first embodiment of the present invention. The apparatus 10 comprises a feeder 12, an agitator 14, a handler 16 and a dispense system 18.

Figure 4:
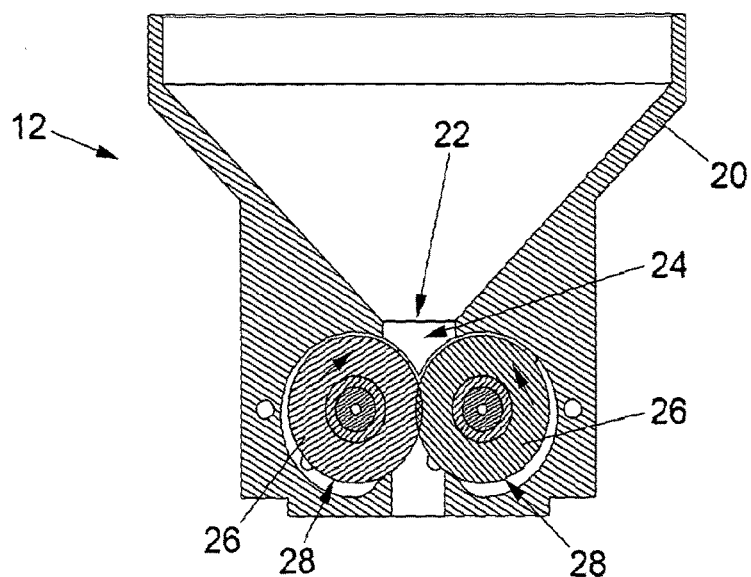
FIG. 4 illustrates a transverse cross-sectional view of the feeder shown in FIG. 1.

The feeder 12 is best shown in FIG. 4 and comprises a low profile plastic hopper 20 configured to accept a pre-sized portion of discrete objects which, in the present case, are provided in the form of melee having an average stone diameter of 3 mm (not shown). In use, the melee will be gently poured into the hopper 20 from a sample pot, parcel or similar vessel and the proportions and material of the hopper 20 have been selected to ensure minimum abrasion between the polished gemstones of the melee.

At the base of the hopper 20 a gap 22 is provided through which the melee will fall into a well provided between a pair of co-operating longitudinal rollers 26. The roller 26 are arranged to rotate in opposite directions so as to gradually draw the melee in the well between and through the rollers 26. The rollers 26 have highly resilient surfaces 28 such that the stones of the melee become embedded in the surfaces 28 without opening a gap between the rollers 26. The speed of the rollers 26 is configured to separate out the stones so that preferably only a single stone is permitted to pass through the feeder 22 at any particular time. This separation ensures that the agitator 14 is not flooded with too many stones at once and reduces the time the stones are in contact with each other to minimise the risk of abrasion.

Further examples of suitable feeders can be found in UK patents GB 2162828, GB 2194518 or GB 2194779.

It is noted that the required speed of the rollers 26 may vary depending on the range of sizes of stones within the melee. Broadly speaking, it is desirable for the melee throughput to be slower for small stones (close to 0.01 ct) and faster for the larger end of the size spectrum (approaching 0.20 ct).

Figure 2:
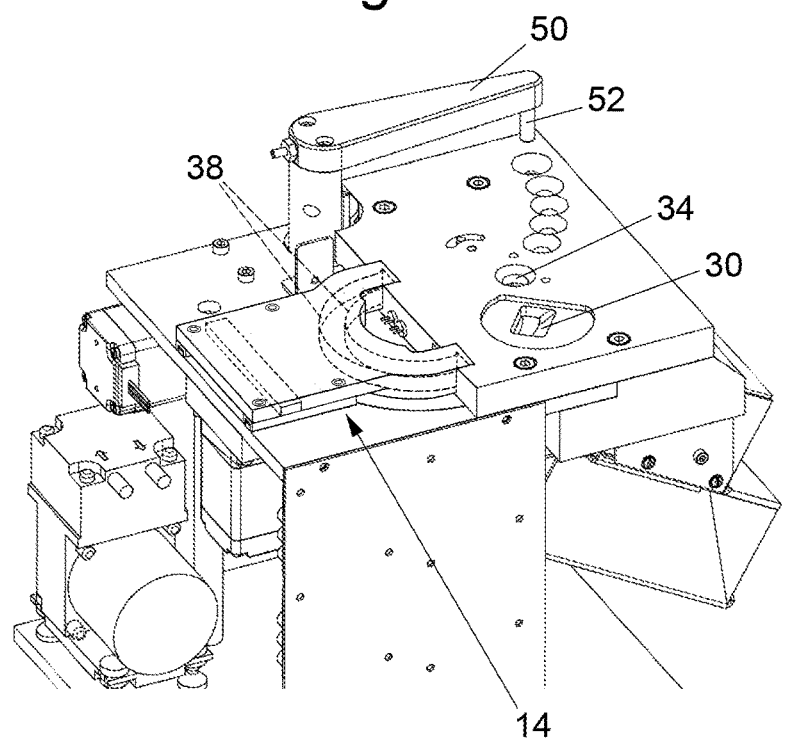
FIG. 2 illustrates a rear perspective view of the apparatus shown in FIG. 1 with the feeder removed and a cover removed to show the oscillating walls and rotating disc.

As the individual stones emerge from the rollers 26, they will fall onto a plastic slope 30, which is provided below the feeder 12 as shown in FIG. 2. The slope 30 will then direct the stones onto a low friction rotating disc 32, shown in FIG. 3, which passes below the end of the slope 30. The rotating disc 32 of the present embodiment is made from fine machined and polished hard plastic to as to provide a suitably low friction co-efficient. However, in other embodiments, the rotating disc 32 may be formed from stainless steel shim.

Figure 5:
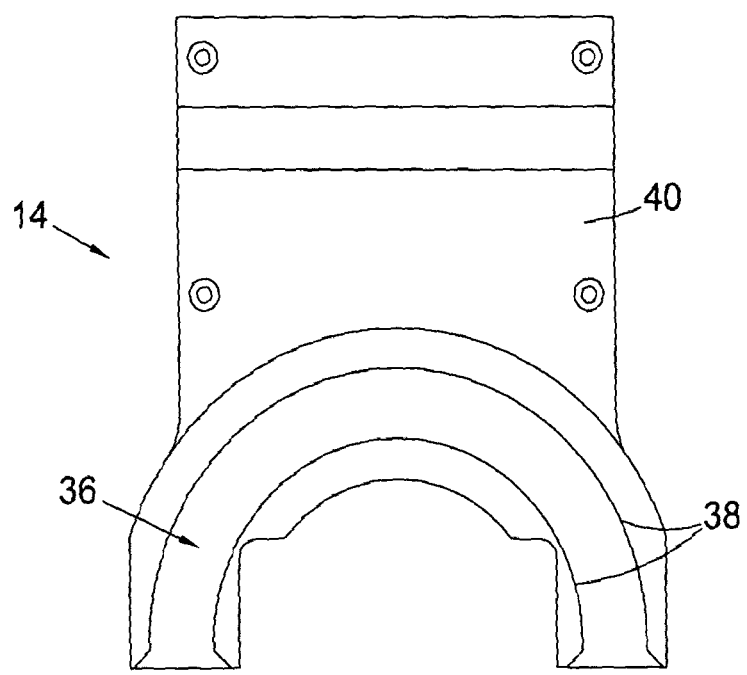
FIG. 5 illustrates a top view of the oscillating wall component shown in FIGS. 2 and 3.

The rotating disc 32 provides a circular travelling path along which the stones are transported at a speed of approximately 924 mm/min to a handling area 34. As viewed in FIG. 3, the rotating disc 32 rotates in a clockwise direction such that the stones are passed through the agitator 14, best shown in FIG. 5. The agitator 14 comprises a pair of opposed parallel vertical walls 38 which form a semi-circular channel 36 over half of the rotating disc 32. The walls 38 therefore extend generally along the direction of the path travelled by the stones on the disc 32. In the embodiment shown, the channel 36 has a width of 9 mm and a length of 45 mm.

The pair of walls 38 are connected to an oscillator 40 configured to oscillate the pair of walls 38 (maintaining their relative positions) in a direction generally transverse to the direction of the travelling path. In the present case, the centre 42 of the pair of walls 38 is configured to oscillate along the radius of the rotating disc 32. Accordingly, the relative traverse movement of the walls 38 across the travelling path is minimal at the entry and exit of the channel 36 and is maximised at the centre of the channel 36.

In use, the oscillating walls 38 collide with the stones on the travelling path. The impact level of the walls 38 is carefully configured so that it is high enough to knock a stone off of a pavilion facet so it lands randomly but not so high as to knock a stone off of its most stable table facet. Accordingly, the stones are repeatedly knocked about within the channel 36 until they eventually land table-down. It is noted that while the stones are moving through the oscillating channel 36, the low friction surface of the rotating disc 32 reduces the possibility of the oscillating channel 36 re-orientating each stone from its table face.

The applicants have found that the optimum impact level is dependent upon at least the following factors: the size of the stones, the width of the channel 36, the stroke length of oscillation, the frequency of oscillation, the speed of transportation through the channel, the channel path and length, and the friction level between the transporting surface and stone. In the present embodiment, they have therefore determined that an oscillation frequency of 4.9 Hz and a stroke length of 14 mm is appropriate.

On exiting the oscillating channel 36, the stones continue their path on the rotating disc 32 until they are aligned in the handling area 34.

Figure 3:
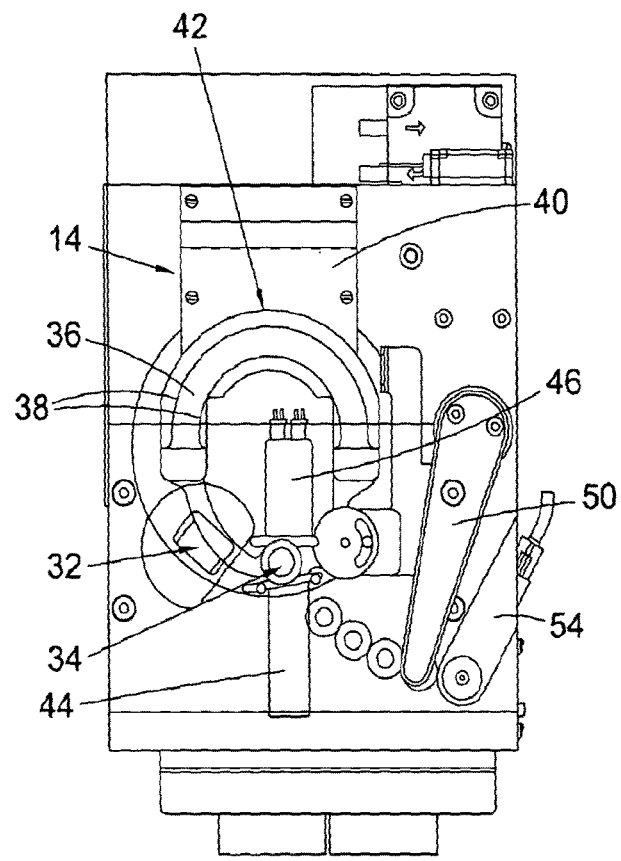
FIG. 3 illustrates a top view of the apparatus shown in FIG. 2.
Figure 6A:
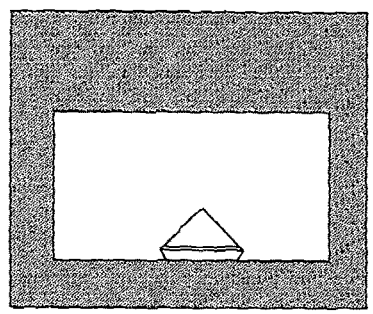
FIG. 6A shows a captured image by the device shown in FIG. 3 for checking the orientation of the objects.

As shown in FIG. 3, a device 44 is provided adjacent the handling area 34, for checking the orientation of the stones. The device 44 comprises a video camera 46 configured to determine when a stone is present in its field of view. When this occurs, the rollers 26, oscillator 40 and rotating disc 32 are all halted so that an image of the stone can be taken (as illustrated in FIG. 6A), and processed by a processor to determine whether the stone is in its desired table-down orientation.

Figure 6B:
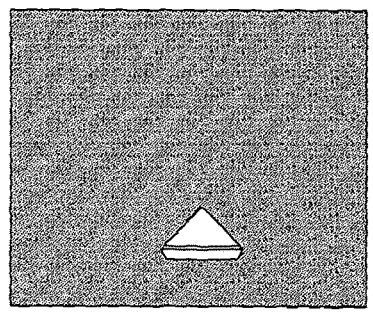
FIG. 6B shows the image of FIG. 6A after a background image has been subtracted.
Figure 6C:
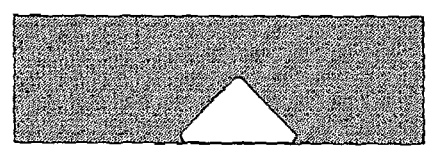
FIG. 6C shows the images of FIG. 6B after it has been converted into a binary silhouette image and cropped to view of the illuminated area.
Figure 6D:
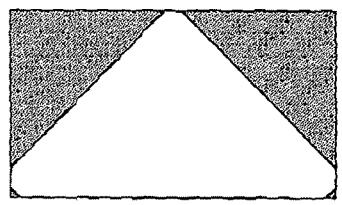
FIG. 6D shows the image of FIG. 6C after the object has been identified as being in the centre of the field of view and after the object has been isolated using its bounding box information.
Figure 7A:
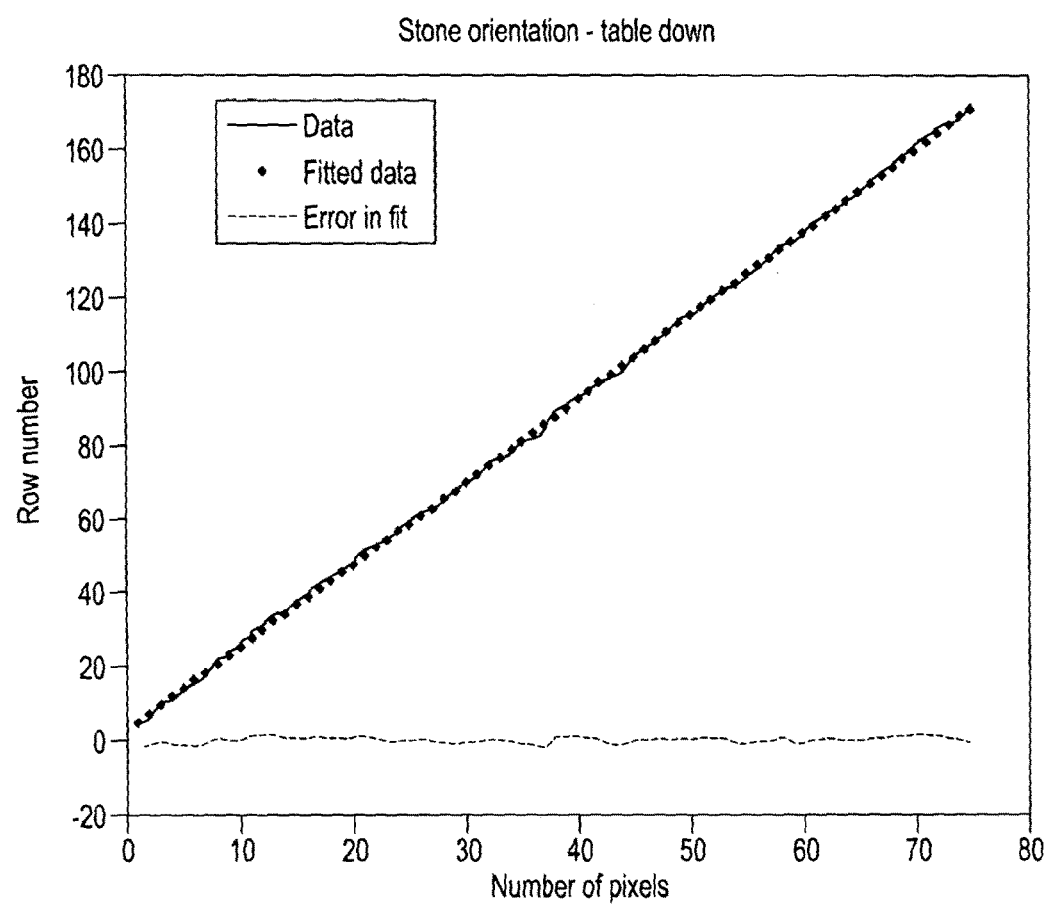
FIG. 7A shows a graph illustrating plotted data of row number against number of pixels making up the object in that row; a line fitted to the data; and the difference between the two plots for a stone which is correctly orientated table-down.
Figure 7B:
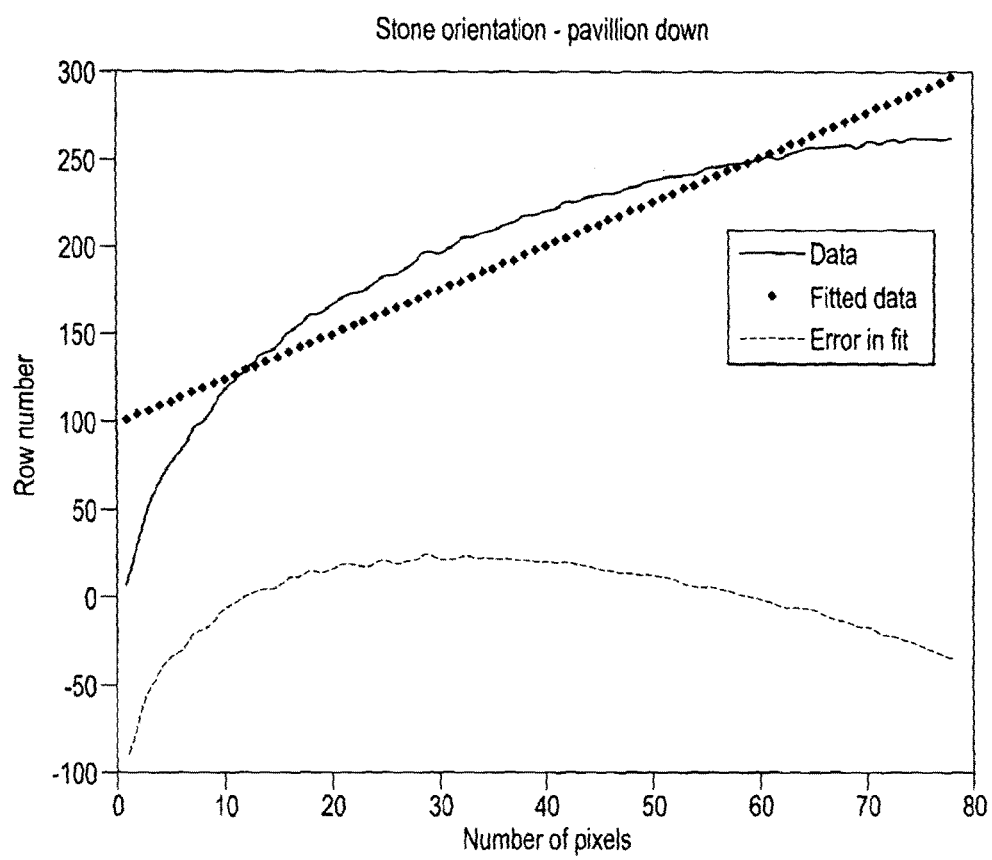
FIG. 7B shows a graph illustrating plotted data of row number against number of pixels making up the object in that row; a line fitted to the data; and the difference between the two plots for a stone which is incorrectly orientated pavilion-down.

More specifically, the video camera 46 records a side view silhouette image of the stones, which is achieved by providing diffuse illumination behind the stones. A background image (with no stone present in the field of view) is recorded at the start of the measurement process. Once a background image is recorded then each captured image (FIG. 6A) from the video camera 46 can be processed as follows:

1) The background image is subtracted from the captured image to produce the image shown in FIG. 6B.
2) The resultant image is cropped to view only the illuminated area.
3) The cropped image is converted into a binary silhouette image, illustrated in FIG. 6C, where the stone area is represented by ones and the background as
4) Each object in the binary silhouette image is identified and the centroid and bounding box calculated.
5) If one of the objects in the binary silhouette image is in the user defined position within the field of view (which corresponds to the required pick-up position for the handler 16) then it is isolated using its bounding box information, as illustrated in FIG. 6D.
6) Once the relevant object has been isolated and cropped the number of white pixels (pixels with a value of one) on each row is calculated. The number of white pixels is then plotted against the row number and a straight line is fitted to the data. Subtracting the fitted data from the actual data gives a measure of the how well the data fits to a straight line. These results are shown in the graph of FIG. 7A (for a stone which is correctly orientated table-down) and in FIG. 7B (for a stone which is incorrectly orientated pavilion-down).
7) If the straight line fit is good (determined by calculating the sum of the squared error and comparing this to a pre-determined threshold value) then the stone is determined to be table-down (FIG. 7A) but if the fit is poor then the stone is determined to be incorrectly orientated (FIG. 7B).

If the stone is found to be orientated on its table, as required, a signal will output which will initiate the automatic collection of the stone by the handler 16, which may be also be referred to as a pick and place arrangement. In the embodiment shown, the handler 16 comprises a swinging arm 50 pivotally mounted on the apparatus 10 and having a vacuum wand 52 provided at its free end. The vacuum wand will be configured to engage with a stone which is orientated table-down and to apply suction to retain the stone on the wand as the arm is pivoted to a new position.

Although the handler 16 may be configured to transport the correctly orientated stones to any test, measurement or further processing system, in the present embodiment, the handler 16 will place the stones on a synthetic detection device 54. The device 54 will determine whether the stone is natural or synthetic before the handler 16 will transport the stone and release it into an appropriate collection bin 56 via chutes 58 in the dispense system 18.

Following the automated collection of a correctly orientated stone, so the rollers 26, oscillator 40 and rotating disc 32 will be re-started and allowed to continue to feed stones through the system until the next stone is transported into the user defined position within the camera's field of vision and the feed system will again stop if the stone is in the correct orientation. Once more the orientation of the stone will be determined and the handler employed if the stone is correctly orientated.

If the stone is found not to be orientated on its table, a signal will recommence the feed system (i.e. rollers 26, oscillator 40 and rotating disc 32) without collecting the stone for measurement. The stone will be therefore be transported once more to the oscillating channel and the agitation process described above will employed to try to re-orientate the stone into the desired position.

The process described above will continue until all stones in the melee have been orientated, measured and dispensed into an appropriate collection bin 56.

It will be appreciated by persons skilled in the art that various modifications may be made to the above embodiments without departing from the scope of the present invention.

The invention claimed is:

1. An apparatus for orientating gemstones, said apparatus comprising:
   a movable surface configured to support said gemstones thereon and provide a travelling path for said gemstones such that the direction of travel of the gemstones is the same as the direction of travel of the movable surface;
   a pair of opposed walls extending generally along the direction of the path; and
   an oscillator arranged to generate relative oscillatory movement between said pair of walls and said movable surface, in a direction generally transverse to the direction of the path, so that, in use, said pair of walls imparts lateral force to the gemstones to thereby urge them into their most stable orientation as they progress along the path while supported on the movable surface;

wherein each gemstone has at least two flat surfaces and the pair of walls imparts sufficient lateral force to urge the gemstones into their most stable orientation on one of the flat surfaces.

2. The apparatus according to claim 1 further comprising a device for checking the orientation of the gemstones after they emerge from between the pair of walls.

3. The apparatus according to claim 1 wherein the movable surface is translatable or rotatable.

4. The apparatus according to claim 3 wherein the movable surface is a rotatable disc.

5. The apparatus according to claim 4 wherein the oscillator is arranged such that a central portion of the pair of walls oscillates along a radial direction of the rotatable disc.

6. The apparatus according to claim 1 wherein the pair of walls are interconnected.

7. The apparatus according to claim 6 wherein the pair of walls are part-toroidal.

8. The apparatus according to claim 1 wherein the oscillator is configured to provide a range of oscillation rates and/or distances or a variable oscillation rate and/or distance.

9. The apparatus according to claim 1 further comprising a feeder for providing the gemstones on the movable surface.

10. The apparatus according to claim 9 wherein the feeder comprises a hopper configured to space out the gemstones along the travelling path so that the risk of the gemstones coming into contact with each other as they are agitated by the oscillator is minimised.

11. The apparatus according to claim 1 further comprising a handler configured for transporting the gemstones from the movable surface after they have passed between the pair of walls at least once.

12. The apparatus according to claim 11 wherein the handler comprises a vacuum wand.

13. The apparatus according to claim 11 wherein the handler is configured to only transport those gemstones identified as being correctly orientated.

14. The apparatus according to claim 11 wherein the handler is configured to transport the gemstones to an appropriate receptacle or collection point.

15. An apparatus for screening for artificial gemstones, said apparatus comprising:
the apparatus for orientating gemstones according to claim 1;
a feeder for providing gemstones on the movable surface;
a test device for determining whether the gemstones are artificial; and
a handler for transporting the gemstones to the test device and subsequently transporting the gemstones to an appropriate receptacle or collection point.

16. The apparatus according to claim 15 further comprising a device for checking the orientation of the gemstones.

17. A method of orientating gemstones comprising:
supporting said gemstones on a surface forming a travelling path;
providing a pair of opposed walls extending generally along the direction of the path; and
generating relative oscillatory movement between said pair of walls and said travelling path, in a direction generally transverse to the direction of the path, so that said pair of walls imparts lateral force to the gemstones to thereby urge them into their most stable orientation as they progress along the path while supported on the surface;
wherein each gemstone has at least two flat surfaces and the pair of walls imparts sufficient lateral force to urge the gemstones into their most stable orientation on one of the flat surfaces.

18. The method according to claim 17 wherein the gemstones are urged into an orientation in which the gemstones have their lowest potential energy.

19. The method according to claim 17 wherein the method comprises orientating the gemstones table-down.

20. The method according to claim 19 wherein each gemstone lies in the range of from approximately 0.01 to approximately 0.20 carats.

21. The method according to claim 17 wherein the travelling path is circular.

22. The method according to claim 21 wherein the relative oscillatory movement is such that a central portion of the pair of walls oscillates along a radial direction of the travelling path.

23. The method according to claim 22 wherein the pair of walls are semi-circular.

24. The method according to claim 17 further comprising the step of checking the orientation of each of the gemstones after the gemstones have emerged from between the pair of walls.

25. The method according to claim 24 wherein the step of checking the orientation of each gemstone comprises:
obtaining an image of the gemstone;
converting the image into a binary silhouette;
plotting the number of pixels representing the gemstone in each row of the silhouette against row number;
fitting an expected curve to the plotted data;
calculating the error between the fitted curve and the plotted data; and
determining whether the error is within a pre-determined threshold denoting that the gemstone is orientated as desired.

26. The method according to claim 25 wherein the expected curve comprises a straight line.

27. The method according to claim 24 further comprising the step of sending the gemstone along the travelling path for a second or subsequent time, if the gemstone is determined not to be orientated as desired.

28. The method according to claim 24 further comprising the step of adjusting the oscillation frequency based on information obtained during the step of checking the orientation of each gemstone.

29. The method according to claim 24 further comprising the step of transporting the gemstones that are orientated as desired to a test, measurement or further processing station.

30. The method according to claim 29 further comprising performing a test, measurement or processing procedure.

31. The method according to claim 30 wherein the procedure may comprise determining whether the gemstone is synthetic or natural.

32. The method according to claim 30 further comprising dispensing the gemstone into an appropriate receptacle depending on the outcome of the procedure.

33. The apparatus according to claim 16, wherein the device for checking the orientation of the gemstones comprises:
an image capture module arranged to obtain an image of the gemstone; and
a processor configured for:
converting the image into a binary silhouette;
plotting the number of pixels representing the gemstone in each row against row number,
fitting an expected curve to the plotted data, calculating the error between the fitted curve and the plotted data; and determining whether the error is within a pre-determined threshold denoting that the gemstone is orientated as desired.

\* \* \* \* \*